(12) United States Patent
Tanaka et al.

(10) Patent No.: US 9,670,311 B2
(45) Date of Patent: Jun. 6, 2017

(54) POLYLACTIC POLYESTER RESIN, AQUEOUS POLYLACTIC POLYESTER RESIN DISPERSION, AND PRODUCTION METHOD FOR AQUEOUS POLYLACTIC POLYESTER RESIN DISPERSION

(71) Applicant: TOYOBO CO., LTD., Osaka (JP)

(72) Inventors: Hideki Tanaka, Shiga (JP); Naoko Oda, Shiga (JP)

(73) Assignee: TOYOBO CO., LTD, Osaka (JP)

( * ) Notice: Subject to any disclaimer, the term of this patent is extended or adjusted under 35 U.S.C. 154(b) by 136 days.

(21) Appl. No.: 14/378,166

(22) PCT Filed: Feb. 18, 2013

(86) PCT No.: PCT/JP2013/053819
§ 371 (c)(1),
(2) Date: Aug. 12, 2014

(87) PCT Pub. No.: WO2013/122245
PCT Pub. Date: Aug. 22, 2013

(65) Prior Publication Data
US 2015/0005174 A1    Jan. 1, 2015

(30) Foreign Application Priority Data

Feb. 17, 2012 (JP) .................................. 2012-032449
Aug. 9, 2012 (JP) .................................. 2012-176994

(51) Int. Cl.
| | | |
|---|---|---|
| *A01N 25/10* | (2006.01) | |
| *C08G 63/08* | (2006.01) | |
| *C08J 3/05* | (2006.01) | |
| *C09D 167/04* | (2006.01) | |
| *C09J 167/04* | (2006.01) | |
| *B32B 27/36* | (2006.01) | |
| *C09D 11/00* | (2014.01) | |
| *C08G 63/664* | (2006.01) | |
| *C09D 11/104* | (2014.01) | |
| *B32B 5/02* | (2006.01) | |
| *B32B 7/06* | (2006.01) | |
| *B32B 7/12* | (2006.01) | |
| *B32B 27/10* | (2006.01) | |
| *B32B 27/12* | (2006.01) | |
| *C08L 101/16* | (2006.01) | |

(52) U.S. Cl.
CPC ............ *C08G 63/08* (2013.01); *A01N 25/10* (2013.01); *B32B 5/022* (2013.01); *B32B 5/024* (2013.01); *B32B 7/06* (2013.01); *B32B 7/12* (2013.01); *B32B 27/10* (2013.01); *B32B 27/12* (2013.01); *B32B 27/36* (2013.01); *C08G 63/664* (2013.01); *C08J 3/05* (2013.01); *C09D 11/00* (2013.01); *C09D 11/104* (2013.01); *C09D 167/04* (2013.01); *C09J 167/04* (2013.01); *B32B 2307/7163* (2013.01); *B32B 2307/748* (2013.01); *B32B 2553/00* (2013.01); *C08J 2367/04* (2013.01); *C08L 101/16* (2013.01); *Y10T 428/3179* (2015.04); *Y10T 442/20* (2015.04)

(58) Field of Classification Search
CPC ............ A01N 25/10; B32B 2307/7163; B32B 307/748; B32B 2553/00; B32B 27/10
See application file for complete search history.

(56) References Cited

U.S. PATENT DOCUMENTS

| | | |
|---|---|---|
| 6,140,458 A | 10/2000 | Terado et al. |
| 6,190,773 B1 | 2/2001 | Imamura et al. |
| 2010/0137526 A1 | 6/2010 | Nakamura et al. |
| 2011/0070320 A1* | 3/2011 | Hahn .................. A61K 9/0043 424/728 |

FOREIGN PATENT DOCUMENTS

| | | |
|---|---|---|
| JP | 8-506848 | 7/1996 |
| JP | 11-43538 | 2/1999 |
| JP | 2000-7789 | 1/2000 |
| JP | 2003-277595 | 10/2003 |
| JP | 2008-13657 | 1/2008 |
| JP | 2008-13658 | 1/2008 |
| JP | 2008-156665 | 7/2008 |
| JP | 2008-222768 | 9/2008 |
| JP | 2010-174170 | 8/2010 |
| WO | 94/19386 | 9/1994 |
| WO | 2008/120722 | 10/2008 |

OTHER PUBLICATIONS

Yun et al. (Macromolecular Research, vol. 16, No. 8, pp. 704-710, Published 2008).*
Feijen et al. (Biomacromolecules, Published 2006, pp. 2790-2795).*
Nektar Advanced PEGylation (Polyethylene Glycol and Derivatives for Advanced PEGylation Catalog 2005-2006, pp. 1-30).*
International Search Report issued May 21, 2013 in International (PCT) Application No. PCT/JP2013/053819.

* cited by examiner

Primary Examiner — Alma Pipic
(74) Attorney, Agent, or Firm — Wenderoth, Lind & Ponack, L.L.P.

(57) ABSTRACT

A polylactic polyester resin having a chemical structure represented by Formula (1), an acid value of 300 to 2,500 eq/$10^6$ g, a number average molecular weight of 2,000 to 50,000, and a lactic acid content percentage of not less than 40 weight %, $$Z-(O-(CH_2CH_2O)_p-(CO-Y-O)_q-X)_r \quad (1)$$

wherein Z is an r-valent organic group, Y is $-CH(CH_3)-$, or a mixture of $-CH(CH_3)-$ and C2-10 linear or branched alkylene group, and X is a residue of a polybasic acid having 2 or more carboxyl groups, or hydrogen; each of X, Y, and Z may be one kind or a mixture of a plurality of different kinds; and p, q, and r are 0 or a positive integer, p has an average value of not less than 0.5, q has an average value of not less than 5, and r has an average value of not less than 3 and not more than 15.

An aqueous dispersion, an aqueous resin composition, an aqueous adhesive, an aqueous paint, aqueous ink, a laminate made of an aqueous adhesive or aqueous ink, a packaging material, a sustained-release biodegradable coating agent, and a sustained-release biodegradable coated body comprising the sustained-release biodegradable coating agent, which contain the polyester resin.

18 Claims, No Drawings

POLYLACTIC POLYESTER RESIN, AQUEOUS POLYLACTIC POLYESTER RESIN DISPERSION, AND PRODUCTION METHOD FOR AQUEOUS POLYLACTIC POLYESTER RESIN DISPERSION

TECHNICAL FIELD

The present invention relates to a polylactic polyester resin having a self-emulsifying function, which enables formation of a stable aqueous emulsion with no emulsifier or organic solvent, and having a resin skeleton derived from a plant raw material. The present invention also relates to a polyester resin aqueous dispersion containing the polylactic polyester resin, and to a method for producing the aqueous dispersion.

BACKGROUND ART

With the recent control of emissions of volatile organic solvents, previously known organic-solvent-based paints, ink, coating agents, adhesives, sealing agents, primers, and agents for treating fiber products and paper products are becoming replaced with aqueous agents, high-solid agents, or powder agents. In particular, the production of aqueous agents using aqueous dispersions ensure good workability and an improved work environment, and thus are considered most versatile and promising. Further, in forming the aqueous dispersion, it is more preferable to use a binder component mainly containing a biodegradable resin in terms of preventing environmental pollution after disposing of the product. It is further preferable to use a binder component that is produced by using a biomass-derived component as a raw material, such as an animal-derived or plant-derived biomass component, in terms of reducing carbon dioxide emissions, compared with a binder component produced from a fossil fuel-derived component.

Polylactic resins are mainly made of a plant-derived component that can be produced from a lactic acid and/or a lactide that can be produced from a plant-derived raw material, such as corn or potato. Polylactic resins are biodegradable and are thus decomposed into water and carbon dioxide in the soil or sea within a few years. Therefore, polylactic resins cause a relatively small environmental burden when emitted into the environment. Thus, if a polylactic resin can be made into an aqueous dispersion, it becomes possible to produce a useful binder component that has biodegradability and is produced from a biomass-derived component. Such a binder component can be expected to be used as a paint, ink, a coating agent, an adhesive, glue, a sealing agent, a primer, an agent for treating a fiber product or a paper product, or the like.

Patent Documents 1 to 5 disclose examples of using a binder component obtained by dispersing a resin containing a polylactic acid segment in water. Patent Documents 1 and 2 disclose polylactic acid aqueous dispersion forcibly emulsified by using an emulsifier. Patent Document 3, which also discloses an aqueous polylactic acid forcibly emulsified by using an emulsifier, discloses that a hydrophilic group may be introduced into the resin, and in particular, sodium salt of 5-sulfoisophthalic acid or sodium salt of dimethyl 5-sulfoisophthalate are preferable in terms of excellent emulsifiability. Patent Document 4 discloses copolymerized polyurethane that has a polylactic acid segment and a segment containing a sulfonic acid metal salt group in the molecule, and has a self-emulsifying function that enables formation of a stable aqueous emulsion without an emulsifier. Further, Patent Document 5 discloses a method for producing self-water dispersible particles by reacting a lactic acid polymer having a hydroxyl group with a polycarboxylic acid or an acid anhydride thereof, thus dissolving the lactic acid polymer in an organic solvent, and then adding a base and water thereto to cause phase-transfer emulsification.

CITATION LIST

Patent Document

Patent Document 1: JP2008-013657A
Patent Document 2: JP2008-013658A
Patent Document 3: JP2003-277595A
Patent Document 4: JP2010-174170A
Patent Document 5: JP2000-007789A

SUMMARY OF INVENTION

Technical Problem

The inventors of the present invention conducted research on the above background art and found the following problems. In the invention of Patent Documents 1, 2, and 3, because the polylactic resin aqueous dispersion is produced by using an emulsifier, when the dispersion is used as a binder component, the adhesiveness decreases because of the emulsifier remaining on the interface of the resin and the object article to which the resin adheres. Further, in the invention in Patent Document 4, a stable aqueous dispersion is obtained without using an emulsifier and thus high adhesiveness is ensured when the dispersion is used as a binder component; however, this method performs solvent removal during the production of the aqueous dispersion, and thus further improvement is necessary in terms of suppressing emissions of volatile organic solvents. Further, in the invention in Patent Document 5, solvent removal was also performed during the production of the aqueous dispersion, and thus further improvement is necessary in terms of suppressing emissions of volatile organic solvents.

The present invention was made in view of the above problems of prior art. Specifically, an object to be attained by the present invention is to provide a polylactic polyester resin that has a self-emulsifying function that enables formation of an aqueous emulsion with no emulsifier or organic solvent, as well as having a high biomass content; and to provide a resin aqueous dispersion composition containing the polylactic polyester resin; an aqueous adhesive composition; aqueous ink; a laminate made of an aqueous adhesive or aqueous ink; a packaging material; and a method for producing an aqueous dispersion.

Solution to Problem

As a result of extensive research, the inventors of the present invention found a means to attain the above object, and accomplished the present invention. Specifically, the present invention has the following features.

Item 1. A polylactic polyester resin having a chemical structure represented by Formula (1), an acid value of 300 to 2,500 eq/$10^6$ g, a number average molecular weight of 2,000 to 50,000, and a lactic acid content percentage of not less than 40 weight %,

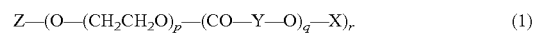

$$Z—(O—(CH_2CH_2O)_p—(CO—Y—O)_q—X)_r \quad (1)$$

wherein Z is an r-valent organic group; Y is —CH(CH$_3$)—, or a mixture of —CH(CH$_3$)— and a C2-10 linear or branched alkylene group; and X is a residue of a polybasic acid having 2 or more carboxyl groups, or hydrogen; each of X, Y, and Z may be one kind or a mixture of a plurality of different kinds; and p, q, and r are 0 or a positive integer, p has an average value of not less than 0.5, q has an average value of not less than 5, and r has an average value of not less than 3 and not more than 15.

Item 2. The polylactic polyester resin according to Item 1, wherein, in Formula (1), —(CO—Y—O)$_q$— is a random copolymer mainly formed of D-lactic acid residue or 6-hydroxycaproic acid residue, or both, and L-lactic acid residue; and the content percentage of L-lactic acid residue in the —(CO—Y—O)$_q$— is not more than 90 weight %.

Item 3. The polylactic polyester resin according to Item 1 or 2, wherein, in Formula (1), Z is a residue of polyhydric alcohol having r or more hydroxyl groups.

Item 4. The polylactic polyester resin according to any one of Items 1 to 3, wherein, in Formula (1), Z is a polyglycerin residue and/or a sorbitol residue.

Item 5. The polylactic polyester resin according to any one of Items 1 to 4, wherein, in Formula (1), X is a residue of one member, or residues of two or more members, selected from the group consisting of trimellitic anhydride, succinic anhydride, and maleic anhydride.

Item 6. A polylactic polyester resin aqueous dispersion comprising the polylactic polyester resin of any one of Items 1 to 5, a basic compound, and water.

Item 7. The polylactic polyester resin aqueous dispersion according to Item 6, wherein the polylactic polyester resin aqueous dispersion does not comprise a surfactant.

Item 8. The polylactic polyester resin aqueous dispersion according to Item 6 or 7, wherein the polylactic polyester resin aqueous dispersion does not comprise an organic solvent.

Item 9. A method for producing a polylactic polyester resin aqueous dispersion, comprising the step of obtaining a polylactic polyester resin aqueous dispersion by mixing the polylactic polyester resin of any one of Items 1 to 5, a basic compound, and water, without adding a surfactant or an organic solvent.

Item 10. An aqueous resin composition comprising the polylactic polyester resin of any one of Items 1 to 5, and a curing agent having a reactivity with respect to a carboxyl group.

Item 11. The aqueous resin composition according to Item 10, wherein the curing agent is one member, or two or more members, selected from the group consisting of polyvalent epoxy compounds, oxazoline resins, carbodiimide resins and polyvalent metal salts.

Item 12. An aqueous adhesive comprising the aqueous resin composition of Item 10 or 11.

Item 13. An aqueous paint comprising the aqueous resin composition of Item 10 or 11.

Item 14. An aqueous ink comprising the aqueous resin composition of Item 10 or 11 and a colorant material.

Item 15. A laminate comprising a layer (Layer A) having the polylactic polyester resin of any one of Items 1 to 5, and a layer (Layer B) selected from the group consisting of films, sheets, woven fabric, non-woven fabric, and paper.

Item 16. The laminate according to Item 15, wherein Layer B mainly comprises a biomass-derived substance and/or a chemically modified biomass-derived substance.

Item 17. A packaging material comprising the laminate of Item 15 or 16 as a component.

Item 18. A sustained-release biodegradable coating agent comprising the aqueous resin composition of Item 10 or 11.

Item 19. A sustained-release biodegradable coated body in which an object substance is coated with the sustained-release biodegradable coating agent according to Item 18.

Item 20. The sustained-release biodegradable coated body according to Item 19, wherein the object substance is a substance having at least one function selected from insecticide, herbicide, sterilization, fungicide, organism attraction, and organism repellency.

Item 21. The sustained-release biodegradable coated body according to Item 19, wherein the object substance has at least one function selected from bioactivity, growth acceleration, and alimentation with respect to an organism.

Advantageous Effects of Invention

Since the polylactic polyester resin of the present invention contains the polylactic acid segment at a high concentration, it has a high biomass content and superior biodegradability. Further, since the polylactic polyester resin of the present invention contains a high concentration of carboxyl groups in the molecular chain, it exhibits superior water dispersibility and thus can be made into an aqueous dispersion simply by being stirred together with an aqueous solution of a basic compound without using an emulsifier and an organic solvent. Further, since the polylactic polyester resin aqueous dispersion of the present invention can thus be prepared without using an emulsifier, it has superior adhesiveness. Further, by adding a curing agent having reactivity with carboxyl group to the polylactic polyester resin aqueous dispersion of the present invention, it is possible to easily obtain an adhesive layer or ink having superior adhesiveness and water resistance. Further, by combining the adhesive and/or ink of the present invention with various biomass materials, it is possible to obtain various laminates having a high biomass content.

DESCRIPTION OF EMBODIMENTS

The polylactic polyester resin of the present invention is a polylactic polyester resin having a chemical structure represented by Formula (1), an acid value of 300 to 2,500 eq/$10^6$ g, a number average molecular weight of 2,000 to 50,000, and a lactic acid content percentage of not less than 40 weight %, $$Z—(O—(CH_2CH_2O)_p—(CO—Y—O)_q—X)_r \qquad (1)$$

wherein Z is an r-valent organic group; Y is —CH(CH$_3$)—, or a mixture of —CH(CH$_3$)— and a C2-10 linear or branched alkylene group; and X is a residue of a polybasic acid having 2 or more carboxyl groups, or hydrogen; each of X, Y, and Z may be one kind or a mixture of a plurality of different kinds; and p, q, and r are 0 or a positive integer, p has an average value of not less than 0.5, q has an average value of not less than 5, and r has an average value of not less than 3 and not more than 15.

The acid value of the polylactic polyester resin of the present invention is not less than 300 eq/ton and not more than 2500 eq/ton, preferably not less than 400 eq/ton and not more than 2300 eq/ton, more preferably not less than 500 eq/ton and not more than 2100 eq/ton. The acid value of the polylactic polyester resin of the present invention is mainly derived from a large number of carboxyl groups at the molecular chain terminal. The polylactic polyester resin of the present invention thereby exhibits a property of forming an aqueous dispersion with no organic solvent or emulsifier ("self-emulsification property", hereinafter), and also provides an effect of forming emulsion particles having a small particle diameter. If the resin acid value is too low, the self-emulsification property of the resin cannot be exhibited, and the curing property of the cured coating film produced from the resin tends to decrease. On the other hand, although an increase in the acid value of the resin tends to increase the water dispersibility, if the acid value is greater than 2500 eq/ton, the water absorbing property of the resin increases, and the resin more easily undergoes hydrolysis even when it is in a solid state; thus, the storage stability of the resin tends to decrease. Further, the water resistance of the cured coating film produced from the resin also tends to decrease.

The number average molecular weight of the polylactic polyester resin of the present invention is preferably not less than 2,000 and not more than 50,000, more preferably not less than 3,000 and not more than 45,000, further preferably not less than 4,000 and not more than 40,000. If the number average molecular weight is too small, the adhesiveness tends to decrease as the cohesive force of the resin decreases. On the other hand, if the number average molecular weight is too large, the cohesive force of the resin increases, and the water dispersibility tends to decrease. Therefore, although it is possible to obtain an aqueous dispersion having a high concentration when an aqueous dispersion is prepared by using a method of first dissolving the resin in a solvent to cause phase transition into an aqueous system, if the aqueous dispersion is prepared by simply mixing a base compound and water, the resulting aqueous dispersion has a very low concentration. Further, when an aqueous dispersion is prepared by simply mixing a base compound and water, the particle diameter tends to excessively increase, thereby causing precipitation immediately after the preparation of the dispersion.

The lactic acid content percentage of the polylactic polyester resin of the present invention is preferably not less than 40 wt %, more preferably not less than 50 wt %, further preferably not less than 60 wt %. If the lactic acid content percentage is less than 40 wt %, the resin has a low biomass content, and thus the resin cannot be considered to be a material that is conducive to large reduction in carbon dioxide emissions and that causes small environmental burden.

The polylactic polyester resin of the present invention can be produced, for example, by causing ring-opening addition polymerization of a cyclic compound having, as a constituent, a lactic acid such as lactide, using, as an initiator, a compound having a structure in which ethylene oxide is added to polyhydric alcohol having at least three hydroxyl groups, and then reacting the terminal hydroxyl groups of the product with a polybasic acid, thereby introducing an acid value into the molecular terminals. The polylactic polyester resin of the present invention can also be produced by causing ring-opening addition polymerization of a cyclic compound, having, as a constituent, a lactic acid such as lactide, and one member or a mixture of two or more members selected from cyclic compounds having, as a constituent, hydroxycarboxylic acid other than lactic acid such as glycolic acid, and lactones such as ε-caprolactone, using, as an initiator, a compound having a structure in which ethylene oxide is added to polyhydric alcohol having at least three hydroxyl groups, and then reacting the terminal hydroxyl groups of the product with a polybasic acid, thereby introducing an acid value in the molecular terminals.

The compound having a structure in which ethylene oxide is added to polyhydric alcohol having at least three hydroxyl groups used as an initiator is a compound having a chemical structure in which ethylene oxide is added to at least one hydroxyl group of the polyhydric alcohol having at least three hydroxyl groups, more preferably, a compound having a chemical structure in which ethylene oxide is added to at least half of the hydroxyl groups of the polyhydric alcohol having four or more hydroxyl groups. The formation of a multibranched structure becomes easier by increasing the number of hydroxyl groups in the initiator. In this manner, it is possible to increase the molecular weight number by using a small amount of initiator. Further, it is also possible to introduce a large acid value by the acid addition, thereby easily ensuring both resin strength and water dispersibility. Examples of polyhydric alcohol having at least three hydroxyl groups to which ethylene oxide is added include trimethylolpropane and glycerin. Further examples of polyhydric alcohols having four or more hydroxyl groups to which ethylene oxide is added include pentaerythritol, diglycerin, polyglycerin, xylitol, sorbitol, glucose, fructose, and mannose. Of these, polyglycerin, xylitol, and sorbitol are preferable because they have a large number of hydroxyl groups.

When the cyclic compound derived from hydroxy acids is subjected to ring-opening addition polymerization reaction using, as an initiator, polyhydric alcohol having a primary hydroxyl group and a secondary hydroxyl group, there is a tendency that, since the reactivity of the secondary hydroxyl group is much lower than the reactivity of the primary hydroxyl group, the primary hydroxyl group is mainly involved in the addition reaction, and the secondary hydroxyl group is not much involved in the addition reaction. Therefore, a branched structure is not easily induced from a secondary hydroxyl group, and a significant effect of increasing the molecular weight and an effect of introducing an acid value cannot be expected. In contrast, by adding ethylene oxide to polyhydric alcohol having a primary hydroxyl group and a secondary hydroxyl group in advance, and using this compound as an initiator, it is effective in that it facilitates production of a branched structure, thus increasing the effect of increasing the molecular weight and the effect of introducing an acid value. In the ethylene oxide addition reaction, the selectivity between the primary hydroxyl group and the secondary hydroxyl group is relatively low; therefore, ethylene oxide is added not only to the primary hydroxyl group but also to some or all of the secondary hydroxyl groups. As a result, some or all of the secondary hydroxyl groups are substituted with —O—$(CH_2CH_2O)_p$—H, and the terminal hydroxyl groups become primary hydroxyl groups. It is preferable to use an initiator in which ethylene oxide is added to all the secondary hydroxyl groups to more easily introduce a branched structure, and to ensure the effect of increasing the molecular weight and introducing an acid value.

In the polylactic polyester resin of the present invention, "p" in the —$(CH_2CH_2O)_p$— is 0 or a positive integer. The average value of p is not less than 0.5. When the average value of p falls below 0.5, the number of segments wherein p is 0 increases, i.e., the number of segments wherein ethylene oxide is not added increases, and thus may increase the proportion of the secondary hydroxyl groups in the initiator. In this case, production of a branched structure is retarded. Consequently, the concentration of the terminal groups in the resin decreases, and the water dispersibility thereby tends to decrease. Further, when a curing agent is added, the reactivity with the curing agent decreases due to the low concentration of the terminal groups, thereby failing to obtain a sufficient three-dimensional crosslinked structure, and the adhesiveness thus tends to decrease. In contrast, the average value of p is preferably not more than 10. If the average value of p is too large, the lactic acid content in the resin relatively decreases, and the biomass content tends to decrease.

In the polylactic polyester resin of the present invention, "Y" is —CH(CH$_3$)—, or a mixture of —CH(CH$_3$)— and a C2-10 linear or branched alkylene group. The —(CO—Y—O)$_q$— can be easily obtained by causing ring-opening addition polymerization of a lactide or a mixture of lactide and lactone using polyol as an initiator. Examples of lactides include lactide (cyclic dimer of lactic acid) and glycolide (cyclic dimer of glycolic acid). Further, examples of lactones include β-propiolactone, β-butyrolactone, pivalolactone, γ-butyrolactone, γ-valerolactone, δ-valerolactone, and ε-caprolactone. These compounds are not necessarily used alone, and a plurality of different kinds can be copolymerized. Of these, ε-caprolactone and lactide that can be easily polymerized and that have excellent biodegradability are preferable.

In the polylactic polyester resin of the present invention, "q" in the —(CO—Y—O)$_q$— is 0 or a positive integer, and the average value of q is not less than 5, more preferably not less than 7, further preferably not less than 10. If the average value of q is too small, the molecular weight of the resulting polylactic polyester resin inevitably decreases, thereby decreasing the cohesive force of the resin; thus, the adhesiveness tends to decrease. On the other hand, the average value of q is preferably not more than 50. When the average value of q is too large, the number average molecular weight of the resin increases, and thus the cohesive force of the resin increases, and relative concentration of X in the resin decreases. This decreases the resin acid value and may thereby decrease water dispersibility.

In the polylactic polyester resin of the present invention, "r" in the —(O—(CH$_2$CH$_2$O)$_p$—(CO—Y—O)$_q$—X)$_r$ is 0 or a positive integer. The average value of r is not less than 3 and not more than 15, more preferably not less than 3.5 and not more than 14, further preferably not less than 4 and not more than 13. If the average value of r is too small, the number of terminal groups in the polymer decreases, thereby decreasing the acid value introduced by the acid addition. Thus, when the resin has a large molecular weight, water dispersibility decreases. If the molecular weight of the resin is decreased to the extent that ensures desirable water dispersibility, the resin strength falls below the practical level. On the other hand, if the average value of r is 15 or more, crosslinking reaction may occur when acids are added to the terminals, thereby turning the resin into a gel.

In the polylactic polyester resin of the present invention, the —(CO—Y—O)$_q$— is preferably a random copolymer mainly formed of D-lactic acid residue or 6-hydroxycaproic acid residue, or both, and L-lactic acid residue. Further, the content percentage of the L-lactic acid residue in the —(CO—Y—O)$_q$— is preferably not more than 90 wt %, more preferably not more than 85 wt %, further preferably not more than 80 wt %. If the content percentage of L-lactic acid is too high, the crystallization property becomes significant, and water dispersibility tends to become insufficient. Further, if the L-lactic acid content exceeds 90 wt %, when the resin is used as an adhesive, its crystallization proceeds with time, and the adhesion strength of the adhesive may thereby significantly decrease.

In the polylactic polyester resin of the present invention, typically, the —(CO—Y—O)$_q$— mainly comprises a random copolymer obtained by ring-opening addition polymerization of D-lactide or ε-caprolactone, or both, and L-lactide. The copolymer may also comprise other components. The random copolymer, which is mainly formed of D-lactide or ε-caprolactone, or both, and L-lactide, can be obtained, for example, by heating and stirring D-lactide or ε-caprolactone, or both, and L-lactide by using polyol as an initiator in the presence or absence of a known ring-opening polymerization catalyst.

In the polylactic polyester resin of the present invention, X is a residue of a polybasic acid having 2 or more carboxyl groups, or hydrogen. Examples of polybasic acid include aromatic dicarboxylic acids such as terephthalic acid, isophthalic acid, orthophthalic acid or naphthalene dicarboxylic acid and acid anhydrides thereof; aliphatic dicarboxylic acids such as succinic acid, glutaric acid, adipic acid, azelaic acid, sebacic acid, dodecanedioic acid, or dimer acid, and acid anhydrides thereof; unsaturated dicarboxylic acids such as maleic acid, fumaric acid, terpene-maleic acid adducts, and acid anhydrides thereof; alicyclic dicarboxylic acids such as 1,4-cyclohexane dicarboxylic acid, tetrahydrophthalic acid, hexahydroisophthalic acid, or 1,2-cyclohexene dicarboxylic acid, and acid anhydrides thereof; and trivalent or higher carboxylic acids such as trimellitic acid, or methylcyclohexene tricarboxylic acid, and acid anhydrides thereof. Of these, trimellitic anhydride is preferable because it can be easily reacted by addition reaction, and also allows introduction of two carboxyl groups per molecule, and thus enables introduction of a large acid value. Therefore, the use of trimellitic anhydride is advantageous in terms of dispersion of resin in water. Further, succinic anhydride, which is a biomass material, is also preferable, because it can be easily reacted, and thus a high biomass content of the resin may be ensured.

Further, as the polybasic acid, it is also possible to use acid dianhydrides such as pyromellitic anhydride (PMDA), oxydiphthalic dianhydride (ODPA), 3,3',4,4'-benzophenonetetracarboxylic dianhydride (BTDA), 3,3',4,4'-diphenyltetracarboxylic dianhydride (BPDA), ethyleneglycol bisanhydrotrimellitate (TMEG), 3,3',4,4'-diphenylsulfonetetracarboxylic dianhydride (DSDA), 4,4'-(hexafluoroisopropylidene)diphthalic dianhydride (6FDA), 2,2'-bis[(dicarboxyphenoxy)phenyl]propane dianhydride (BSAA), or glycerin trisanhydrotrimellitate. By using these compounds, the molecular weight is increased by a chain extension effect. It is thus preferable in terms of increase in resin strength. Ethyleneglycol bisanhydrotrimellitate (TMEG) is particularly preferable because it can undergo an addition reaction at a relatively low temperature, and has a small cohesive force and excellent water dispersibility.

The polylactic polyester resin of the present invention can be produced, for example, by performing ring-opening addition polymerization of lactide and ε-caprolactone using polyol having 3 or more hydroxyl groups as an initiator, and then performing an addition reaction of the terminal hydroxyl groups of the product with a polybasic acid. More specifically, polyol having 3 or more hydroxyl groups, lactide, ε-caprolactone, and a catalyst are heated together to a temperature of not less than 150° C., thereby advancing the polymerization for 1 to 3 hours; thereafter, polybasic acid anhydride is added thereto and reacted for 1 to 2 hours, thereby obtaining the polylactic polyester resin of the present invention. In order to prevent ring-opening of the polybasic acid anhydride as it is reacted with water in the polymerization system, it is preferable to decrease the moisture content of the materials in advance by vacuum drying or the like. Further, in order to avoid the influence of moisture during the polymerization, it is preferable to perform polymerization in a vacuum or under an inert gas atmosphere. The polymerization temperature is preferably not more than 180° C. by taking into consideration the thermal stability of polylactic acid. Further, by using a known acid addition catalyst, it is possible to increase the polymerization speed. Examples of catalysts include amines such as triethylamine or benzyldimethylamine; quaternary ammonium salts such as tetramethylammonium chloride or triethylbenzylammonium chloride; imidazoles such as 2-ethyl-4-imidazole; pyridines such as 4-dimethylaminopyridine; phosphines such as triphenylphosphine; phosphonium salts such as tetraphenylphosphonium bromide; sulfonium salts such as sodium p-toluenesulfonate; sulfonic acids such as p-toluenesulfonic acid; and organic metal salts such as zinc octylate. Of these, more preferable examples include amines, pyridines, and phosphines. In particular, by using 4-dimethylaminopyridine, the polymerization speed can be increased.

It is effective to add various antioxidants in the polymerization of the polylactic polyester resin of the present invention. When the polymerization temperature is high, or when the polymerization time is long, the polylactic acid segments may be colored due to oxidation degradation due to their low heat resistance. Further, when a segment with low heat resistance such as polyether is copolymerized, the polylactic acid segments become more susceptible to oxidation degradation. In this case, addition of antioxidant is particularly effective. Examples of antioxidants include known antioxidants such as phenol-based antioxidants, phosphorus-based antioxidants, amine-based antioxidants, sulfur-based antioxidants, nitro compound-based antioxidants, or inorganic compound-based antioxidants. It is preferable to use a phenol-based antioxidant having relatively high heat resistance. The amount of the antioxidant is preferably not less than 0.05 wt % and not more than 0.5 wt % relative to the resin.

Since the polylactic polyester resin of the present invention has superior water dispersibility, it can be easily dispersed in warm water in the presence of a basic compound. The liquid temperature during the production of the aqueous dispersion is preferably not less than 30° C. and not more than 85° C., more preferably not less than 40° C. and not more than 80° C., further preferably not less than 45° C. and not more than 75° C. Although the dispersion is advanced even under a low water temperature, it takes a longer time. The dispersion is accelerated by an increase in water temperature; however, if the water temperature is too high, the hydrolysis of the polylactic polyester resin tends to be accelerated, and the molecular weight of the polylactic polyester resin of the present invention tends to decrease.

Examples of basic compounds used in the production method of the polylactic polyester resin aqueous dispersion of the present invention include ammonia, organic amine compounds, and inorganic basic compounds.

Examples of the organic amine compounds include alkylamines such as triethylamine, isopropylamine, ethylamine, diethylamine, or sec-butylamine; alkoxyamines such as 3-ethoxypropylamine, propylamine, or 3-methoxypropylamine; alkanolamines such as N,N-diethylethanolamine, N,N-dimethylethanolamine, aminoethanolamine, N-methyl-N,N-diethanolamine, monoethanolamine, diethanolamine, or triethanolamine; and morpholines such as morpholine, N-methylmorpholine, or N-ethylmorpholine. Of these, using alkanolamines having high hydrophilicity, in particular, triethanolamine, enables increasing the water dispersibility.

Specific examples of the inorganic basic compound include alkali metal hydroxides such as lithium hydroxide, sodium hydroxide, or potassium hydroxide; alkali metal carbonates or hydrogen carbonates such as sodium hydrogen carbonate or sodium carbonate, and ammonium carbonate.

The basic compounds of polyvalent metals may generate salts insoluble in water with the plurality of carboxyl groups contained in the polylactic polyester resin of the present invention, and thereby may decrease the dispersibility. Thus, if a basic compound of polyvalent metal is used, it is preferable to use it only in a small amount.

It is necessary to use the basic compound in an amount that enables neutralization of at least one of the carboxyl groups in the polylactic polyester resin of the present invention. Specifically, it is preferable to add 0.5 to 1.0 equivalent of the basic compound based on the acid value of the polylactic polyester resin of the present invention. Further, it is also possible to form an aqueous dispersion using less than 1.0 equivalent of a basic compound based on the acid value of the polylactic polyester resin of the present invention, and then add more basic compound to make the final addition amount of the basic compound 0.5 to 1.0 equivalent based on the acid value. In this case, the pH of the aqueous dispersion is preferably adjusted to 6.5 to 7.0 so as to suppress the hydrolysis of the polylactic acid segments. If the proportion of the basic compound to be added is too low, water dispersibility tends to decrease. If the proportion of the basic compound to be added is too high, the pH of the aqueous dispersion increases and may cause hydrolysis of the polylactic polyester resin.

The production of the aqueous dispersion of the polylactic polyester resin of the present invention does not require an emulsifier or an organic solvent; however, the present invention does not exclude the use of these agents. By using various nonionic emulsifiers or anionic emulsifiers, it may become possible to further increase the stability of the aqueous dispersion. Further, by first dissolving the polylactic polyester resin of the present invention in an appropriate organic solvent, and then causing phase transition, it may become possible to obtain a more stable aqueous dispersion.

The polylactic polyester resin aqueous dispersion of the present invention may be used as an adhesive. When the polylactic polyester resin aqueous dispersion of the present invention is used as an adhesive, it is possible to obtain an adhesive with high adhesion strength by adding a curing agent that reacts with carboxyl group. Examples of the curing agent include amino resins such as melamine or benzoguanamine-based resin, polyvalent isocyanate compounds, polyvalent oxazoline compounds, polyvalent epoxy compounds, and phenol resin. In particular, polyvalent epoxy compounds and polyvalent oxazoline compounds are preferable because they are highly reactive with carboxyl group, and thus enable low temperature curing, thereby ensuring high adhesion strength. Further, polyvalent metal salts may also be used as a curing agent.

When these curing agents are used, their content is preferably 5 to 50 parts by mass, per 100 parts by mass of the polylactic polyester resin of the present invention. If the content of the curing agent falls below 5 parts by mass, the curing property tends to become insufficient. If the content of the curing agent exceeds 50 parts by mass, the resulting coating film tends to become too hard.

Examples of appropriate epoxy compound as the curing agent for the aqueous adhesive of the present invention include novolac epoxy resin, bisphenol-type epoxy resin, trisphenolmethane-type epoxy resin, amino-group-containing epoxy resin, and copolymerization-type epoxy resin. Examples of novolac epoxy resin include resins obtained by reacting a novolac resin obtained by reacting a phenol such as phenol, cresol, or alkylphenol with formaldehyde in the presence of an acid catalyst with epichlorohydrin and/or methylepichlorohydrin. Examples of bisphenol-type epoxy resin include resins obtained by reacting bisphenols such as bisphenol A, bisphenol F, or bisphenol S with epichlorohydrin and/or methylepichlorohydrin, and resins obtained by reacting a condensation product of diglycidyl ether of bisphenol A and the aforementioned bisphenol with epichlorohydrin and/or methylepichlorohydrin. Examples of trisphenolmethane-type epoxy resin include resins obtained by reacting trisphenolmethane, triscresolmethane or the like with epichlorohydrin and/or methylepichlorohydrin. Examples of amino-group-containing epoxy resin include glycidylamine-based resins such as tetraglycidyldiaminodiphenylmethane, triglycidyl para-aminophenol, tetraglycidylbisaminomethylcyclohexanone, or N,N,N',N'-tetraglycidyl-m-xylenediamine. Examples of copolymerization-type epoxy resin include a copolymer of glycidyl methacrylate and styrene; a copolymer of glycidyl methacrylate, styrene, and methyl methacrylate; and a copolymer of glycidyl methacrylate and cyclohexylmaleimide.

Since the polylactic polyester resin aqueous dispersion of the present invention has an emulsification effect, it is possible to use an epoxy compound, which is insoluble in water, as a curing agent. However, water-soluble epoxy resin can be more easily used and is thus more preferable. Examples of water-soluble epoxy resin include resins obtained by substituting one or more of the hydroxyl groups of a water-soluble compound, such as polyethylene glycol, glycerin and a derivative thereof, or sorbitol, with glycidyl groups. Examples of commercially available water-soluble epoxy resins include SR-EGM, SR-8EG, SR-GLG, and SR-SEP (Sakamoto Yakuhin Kogyo, Co., Ltd), and Denacol EX-614, EX-512, and EX-412 (Nagase ChemteX Corporation).

Examples of appropriate oxazoline compounds to be used as a curing agent for the aqueous adhesive of the present invention include commercially available oxazoline compounds, such as Epocros WS-500, WS-700, Epocros K-2010E, or Epocros K-2020E (Nippon Shokubai Co., Ltd.).

Examples of appropriate carbodiimide compounds to be used as a curing agent for the aqueous adhesive of the present invention include commercially available carbodiimide compounds, such as Carbodilite V-02 or Carbodilite V-04 (Nisshinbo Holdings Inc).

Examples of appropriate polyvalent metal salts to be used as a curing agent for the aqueous adhesive of the present invention include calcium salts, zinc salts, and aluminum salts. In particular, calcium chloride and ammonium zinc carbonate are preferable.

Examples of appropriate phenol resin to be used as a curing agent for the aqueous adhesive of the present invention include condensation products of alkylated phenol and/or cresol and formaldehyde. Specifically, examples include condensation products of alkylated phenols obtained by alkylating a phenol with an alkyl group such as methyl, ethyl, propyl, isopropyl, or butyl; p-tert-amylphenol; 4,4'-sec-butylidenephenol; p-tert-butylphenol; o-cresol; m-cresol; p-cresol; p-cyclohexylphenol; 4,4'-isopropylidenephenol; p-nonylphenol; p-octylphenol; 3-pentadecylphenol; phenol; phenyl-o-cresol; p-phenylphenol; xylenol, and the like; and formaldehyde.

Examples of appropriate amino resin to be used as a curing agent for the aqueous adhesive of the present invention include adducts of urea, melamine, benzoguanamine, or the like with formaldehyde; and alkyl ether compounds obtained by alkoxylating these compounds with a C1-6 alcohol. Examples include methoxylated methylolurea, methoxylated methylol-N,N-ethyleneurea, methoxylated methyloldicyandiamide, methoxylated methylolmelamine, methoxylated methylolbenzoguanamine, butoxylated methylolmelamine, and butoxylated methylolbenzoguanamine. Of these, methoxylated methylolmelamine, butoxylated methylolmelamine, and methylolated benzoguanamine are preferable. They may be used solely or in a combination of two or more.

Examples of appropriate isocyanate compounds to be used as a curing agent for the aqueous adhesive of the present invention include low-molecular-weight compounds and high-molecular-weight compounds. Examples of low-molecular-weight compounds include aliphatic isocyanate compounds such as tetramethylene diisocyanate, hexamethylene diisocyanate, or xylylene diisocyanate; aromatic isocyanate compounds such as toluene diisocyanate or diphenylmethane diisocyanate; alicyclic isocyanates such as hydrogenated diphenylmethane diisocyanate, hydrogenated xylylene diisocyanate or isophorone diisocyanate; and trimers of these isocyanate compounds. Examples of high-molecular-weight compounds include compounds having one or more terminal isocyanate groups obtained by reacting a compound having a plurality of active hydrogens with an excess amount of the above low-molecular-weight polyisocyanate compound. Examples of the compound having a plurality of active hydrogens include polyhydric alcohol compounds such as ethylene glycol, propylene glycol, trimethylolpropane, glycerin, or sorbitol; polyamine compounds such as ethylenediamine; compounds having hydroxyl group and amino group such as monoethanolamine, diethanolamine, or triethanolamine; and polymers containing active hydrogens such as polyester polyol, polyether polyol, or polyamide.

Examples of isocyanate compounds include blocked isocyanates. Examples of isocyanate blocking agents include phenol compounds such as phenol, thiophenol, methylthiophenol, cresol, xylenol, resorcinol, nitrophenol, or chlorophenol; oxime compounds such as acetoxime, methyl ethyl ketoxime, or cyclohexanone oxime; alcohols such as methanol, ethanol, propanol or butanol; halogen substituted alcohols such as ethylenechlorohydrine, or 1,3-dichloro-2-propanol; tertiary alcohols such as t-butanol or t-pentanol; lactams such as ε-caprolactam, δ-valerolactam, γ-butyrolactam, or β-propyllactam; aromatic amines; imides; active methylene compounds such as acetylacetone, acetoacetic ester, or ethyl malonate; mercaptans; imines; ureas; diaryl compounds; and sodium bisulfite. The blocked isocyanate is obtained by subjecting the isocyanate compound and the isocyanate blocking agent to an addition reaction using a known suitable method.

An aqueous ink can be obtained by incorporating a colorant material in the polylactic polyester resin aqueous dispersion of the present invention. Further, the water resistance of the ink can be increased by adding a curing agent having reactivity with respect to carboxyl group to the ink. Examples of the colorant material to be added include known pigments and dyes. Since the polylactic polyester resin of the present invention is a polyester resin having a large acid value, high dispersibility of the pigment is ensured. Thus it is possible to prepare highly concentrated aqueous ink. The curing agent used herein may be selected from those used for the adhesives.

It is possible to obtain an aqueous paint by incorporating various pigments and additives generally used for paints to the polylactic polyester resin aqueous dispersion of the present invention. Further, it is possible to improve the water resistance of the resulting coating film by incorporating a curing agent having reactivity with carboxyl group. Examples of pigments include known organic/inorganic color pigments, extenders such as calcium carbonates or talc, rust preventive pigments such as red lead or lead suboxide, and various functional pigments such as aluminum powder or zinc sulfide (fluorescent pigments). Examples of the additives include plasticizers, dispersants, precipitation inhibitors, emulsifiers, thickeners, antifoaming agents, antifungal agents, preservatives, anti-skinning agents, anti-sagging agents, matting agents, antistatic agents, conducting agents and flame retardants. Since the polylactic polyester resin of the present invention is a polyester resin having a large acid value, high dispersibility of the pigment is ensured. It is thus possible to prepare highly concentrated aqueous paint. The curing agent used herein may be selected from those used for the adhesives.

By adding various thickeners, the aqueous dispersion, the aqueous adhesive, the aqueous ink, and the aqueous paint of the present invention may have viscosity characteristics and a viscosity degree suited to the workability. Considering the stability of the system by the addition of the thickener, nonionic thickeners such as methylcellulose or polyalkylene glycol derivative, and anionic thickeners such as polyacrylic acid salt or alginic acid salt are preferable.

By adding various surface tension regulators, the coating property of the aqueous dispersion, the aqueous adhesive, the aqueous ink, and the aqueous paint of the present invention can be further improved. Examples of surface tension regulators include acrylic, vinyl, silicone, and fluorine-based surface tension regulators. Particularly preferable examples include, but are not limited to, acrylic and vinyl surface tension regulators because of their ability to maintain the adhesiveness. If the amount of the surface tension regulator to be added is too large, the adhesion strength tends to decrease. Thus, the amount of the surface tension regulator is preferably not more than 1 wt %, more preferably not more than 0.5 wt %, based on the amount of the resin.

Other known additives, such as surface-smoothing agents, antifoaming agents, antioxidants, dispersants, or lubricants, may be also added during the production of the aqueous dispersion of the present invention. They may otherwise be added to the obtained aqueous dispersion.

The light resistance and oxidation resistance of the aqueous dispersion, the aqueous adhesive, the aqueous ink, and the aqueous paint of the present invention can be further improved by adding various UV absorbers, antioxidants, or light stabilizers. It is possible to greatly improve light resistance by introducing a compound having an ultraviolet absorption effect and a light stabilization effect to the polyester skeleton. Further, it is possible to improve the weather resistance by adding an emulsion or an aqueous solution of a UV absorber, an antioxidant, or a light stabilizer to the polyester resin aqueous dispersion. Examples of UV absorbers include benzotriazole-based, benzophenone-based, triazine-based and various similar organic UV absorbers; and zinc oxide or other inorganic UV absorbers. Further, examples of antioxidants include various antioxidants generally used for polymers, such as hindered phenol, phenothiazine, or nickel compound. Examples of light stabilizers include various light stabilizers generally used for polymers. A hindered amine-based light stabilizer is effective.

A laminate can be formed by laminating a layer (Layer A) having the polylactic polyester resin of the present invention, and a layer (Layer B) selected from the group consisting of films, sheets, woven fabric, non-woven fabric and paper. The laminate can be easily obtained, for example, by applying the aqueous adhesive and/or aqueous ink of the present invention on Layer B selected from the group consisting of films, sheets, woven fabric, non-woven fabric and paper, and drying the adhesive and/or ink. The aqueous adhesive and the aqueous ink of the present invention have strong adhesiveness with respect to a film, a sheet, woven fabric, non-woven fabric and paper made of various materials. The aqueous adhesive and the aqueous ink of the present invention particularly have strong adhesiveness with respect to a film and a sheet made of polylactic acid, polyester, polyurethane, polyamide, cellulose, starch, vinyl chloride, vinylidene chloride, chlorinated polyolefin and chemically modified substances thereof. Of these, by combining the adhesive and/or ink with a film, a sheet, or a paper made of a biomass material such as polylactic acid, cellulose, or starch, it is possible to significantly increase the biomass content of the entire laminate. Further, the aqueous adhesive and the aqueous ink of the polylactic polyester resin of the present invention exhibit strong adhesiveness also with respect to various metal vapor-deposited films, and thus it is possible to use the adhesive and the ink to construct a three-layer laminate consisting of Layer A, a metal vapor-deposited layer, and Layer B. The metal used for the metal vapor-deposited layer and Layer B are not particularly limited; however, the aqueous adhesive and the aqueous ink of the polylactic polyester resin of the present invention ensure a large adhesion strength particularly with respect to an aluminum vapor-deposited film. The adhesion strength of the aqueous adhesive and the aqueous ink of the polylactic polyester resin of the present invention with respect to various metal vapor-deposited films is assumed to be due to the high acid value of the polyester resin of the present invention. Since these laminates have a high biomass content, they are preferably used as a material that is discarded in a relatively short time, for example, a packaging material. In particular, they are best used as a food packaging material.

The polylactic polyester resin of the present invention and the aqueous dispersion thereof may be used as a sustained-release biodegradable coating agent. The polylactic resin of the present invention is biodegraded at an appropriate speed and is thus gradually biodegraded over a long period of time when it is exposed to the natural environment while gradually emitting the object component coated with the resin to the environment. Therefore, a coated body obtained by coating an object substance, such as a fertilizer, an agricultural chemical, a fungicide, a sterilizer, or an organism repellent agent, with the biodegradable coating agent of the present invention has superior sustained-release characteristics of the object substance. Further, in a preferred embodiment, the biodegradable coating agent of the present invention can be made into an aqueous dispersion having superior film-forming characteristics, and can thus be used in the form of a coating film.

Sustained-Release Biodegradable Coated Body

The sustained-release biodegradable coated body of the present invention is obtained by coating an object substance with a sustained-release biodegradable coating agent of the present invention. The sustained-release biodegradable coated body of the present invention may contain a component or components other than the substance to be coated and the sustained-release biodegradable coating agent of the present invention, for example, other biodegradable resins, non-biodegradable resins, hydrolysis promoters, hydrolysis inhibitors, and the like. Further, the sustained-release biodegradable coated body, which refers to an article in which an object substance is coated with a sustained-release biodegradable coating agent, also includes a coated body having the same substance as the object substance inside the coated body and also on its outer surface.

The sustained-release biodegradable coated body of the present invention has an effect of being gradually degraded by microorganisms or other organisms in the natural environment, such as the surface of or inside soil, rivers, lakes and oceans, while continuously emitting the contained object substance for a long period of time. Therefore, by selecting an appropriate substance, the sustained-release biodegradable coated body of the present invention may be used as a sustained-release agricultural chemical, a slow-release fertilizer, or a sustainable antifouling paint.

Substance to be Coated

The substance to be coated in the present invention is not particularly limited insofar as its release to the natural environment can be controlled. Examples of the substance to be coated in the present invention include a substance having a function of exterminating organisms, such as a function of insecticide, herbicide, sterilization, fungicide, organism attraction, organism repellency, and the like; and a substance that can be expected to have a function of growth promotion and/or alimentation of organisms such as bioactive substances or fertilizers. The substance to be coated may be composed of a single component or a plurality of components.

Method for Producing Sustained-Release Biodegradable Coated Body

The method for producing the sustained-release biodegradable coated body of the present invention is not particularly limited; however, the coated body of the present invention is preferably produced from the polylactic polyester resin aqueous dispersion of the present invention because production is easier in this manner. Specifically, the biodegradable coated body can be obtained by using a method of dissolving or dispersing the object substance to be coated in the aqueous dispersion, atomizing the resulting dispersion, and evaporating the moisture to obtain particles; a method of spraying the dispersion in the presence of a carrier, thereby adhering the dispersion to the surface and/or the inside of the carrier; or a method of applying the dispersion to a base body to form a coating film thereon. Moreover, when the polylactic biodegradable resin has a self-emulsification property, i.e., the property of forming an aqueous dispersion without a surfactant, it is not necessary to emit a surfactant to the environment during the biodegradation. This is more preferable because the environmental burden can be further reduced. Moreover, when the aqueous dispersion contains only a small amount of organic solvent or is completely free of organic solvent, the emission of organic solvent to the environment during the production or the use of the coated body can be reduced or prevented. This is more preferable because the environmental burden can be further reduced.

EXAMPLES

Hereunder, the present invention is more specifically described with reference to Examples. However, the present invention is not limited to these examples, and various modifications may be appropriately made within the scope of the present invention. Such modifications are also included in the technical scope of the present invention.

Unless otherwise specified, "part" means a part by weight. Further, the measurement and evaluation methods used in the specification are as follows.

Resin Formulation

A resin sample was dissolved in a deuterated chloroform or deuterated dimethyl sulfoxide, and subjected to $^1$H-NMR analysis and $^{13}$C-NMR analysis using a 400-MR NMR device (Varian Inc.). According to the obtained integration ratio, the resin formulation was found and shown in wt %. Further, based on this resin formulation, lactic acid content percentage (wt %), and the values p, q, and r were calculated.

L-Lactic Acid Content

A chloroform solution of a resin sample (5 g/100 mL) was prepared, and the specific optical rotation was measured at a light-source wavelength of 589 nm at a temperature of 25° C., thereby finding [α]obs. Further, a resin was polymerized so that it had the same formulation as in the above sample, except that all of the lactic acid components were substituted with L-lactic acid components. Then the specific optical rotation of the resin was measured in the same manner as for finding [α]obs, thereby finding [α]100.

$$OP[\%]=ABS([\alpha]obs/[\alpha]100)*100$$

When OP is 100%, the lactic acids contained in the sample are all L-lactic acids. When OP is 0%, the proportion of L-lactic acid and D-lactic acid are both 50%, and the following relation is satisfied.

$$\text{L-lactic acid}/(\text{L-lactic acid}+\text{D-lactic acid})=50+[OP]/2$$

With this equation, the ratio of L-lactic acid to D-lactic acid was found, and then the L-lactic acid content percentage was calculated in consideration of the lactic acid content percentage separately found by using the above method.

Number Average Molecular Weight

A resin sample was dissolved in tetrahydrofuran so that the resin concentration was about 0.5 wt %, and subjected to filtration using a polytetrafluoroethylene membrane filter having a pore diameter of 0.5 μm. Using this sample as a measurement sample, the molecular weight was measured by gel permeation chromatography (GPC) using a differential refractometer as a detector, and tetrahydrofuran as a mobile phase. The flow rate was 1 mL/min, and the column temperature was 30° C. KF-802, 804L, and 806L (Showa Denko K.K.) were used as the columns. The monodisperse polystyrene was used as the molecular weight standard.

Acid Value 0.8 g of a resin sample was dissolved in 20 ml N,N-dimethylformamide and subjected to titration using a 0.1N sodium methoxide-methanol solution in the presence of phenolphthalein as an indicator. The point of neutralization was determined by the color change of the solution into red, and the value was converted into an equivalent amount per $10^6$ g of resin (equivalent/$10^6$ g).

Storage Stability

After the resin sample was stored for 10 days at 50° C., the number average molecular weight was measured, and the change in molecular weight was evaluated.

Classification

A: The change in number average molecular weight was less than 5%.

B: The change in number average molecular weight was not less than 5% and less than 10%.

C: The change in number average molecular weight was 10% or more.

Evaluation of Water Dispersibility

A resin, a basic compound, and water, each in a predetermined amount, were mixed. Thereafter, the system was stirred at 400 rpm while keeping the temperature at 60° C.

The water dispersibility was determined by visual inspection.

Classification
A: The resin was completely dispersed without generating undispersed matter.
B: Undispersed matter was observed.
C: The resin was not dispersed at all.

Average Particle Diameter of Aqueous Dispersion

The arithmetic volume-based average particle diameter of the aqueous dispersion sample was measured using a Horiba LB-500. The measured value was used as the average particle diameter of the aqueous dispersion. However, the measurement of the average particle diameter was not performed for samples having a water dispersibility of B or C. The average particle diameters of these samples are expressed with a dash in the table.

Preparation of Aqueous Adhesive

A water-soluble epoxy resin SR-SEP (Sakamoto Yakuhin Kogyo Co., Ltd.) was added as a curing agent to the aqueous dispersion at the proportion shown in Table 3, thereby preparing an aqueous adhesive.

Preparation of Sample for Evaluation of Adhesiveness

An aqueous adhesive was applied onto a corona-treated surface of a PET film (Toyobo Co., Ltd) having a thickness of 25 μm so that the thickness of the adhesive after drying was 5 μm, and dried at 80° C. for 5 minutes. A corona-treated surface of a second PET film having a thickness of 25 μm was bonded to the adhesive-applied surface of the first PET film. The resulting laminate was pressed at 80° C. for 30 seconds under a pressure of 3 kgf/cm². The laminate was then cured by heat at 40° C. for 8 hours, thereby obtaining a sample for peel strength evaluation (sample for initial evaluation).

Evaluation of Adhesiveness

The peel strength was measured to evaluate the adhesiveness. A 180° peel test was performed at 25° C. with a tensile rate of 300 mm/min, thereby measuring the peel strength. To ensure practical performance, the peel strength is preferably not less than 2 N/cm. For samples having water dispersibility of B or C, aqueous adhesives were prepared using supernatant liquids of those samples, and these adhesives were applied on films so as to create samples for adhesiveness evaluation; however, because they contain only a small amount of active ingredient, the application could not form a layer having a dried thickness of 5 μm. Therefore, for these samples, samples for adhesiveness evaluation were prepared with an adhesive only in an applicable amount, and the peel strength of each sample was measured. The peel strength was not more than 0.1/cm, showing that an accurate measurement was not possible. The evaluations of these samples are expressed with a dash in the table.

Evaluation of Water Resistance

Each sample for the evaluation of adhesiveness was immersed in water of 25° C. for 5 hours. Thereafter, the water in the sample surface was fully removed, and a 180° peel test was performed at 25° C. with a tensile rate of 300 mm/min, thereby measuring the peel strength. Since samples having water dispersibility of B or C had almost no adhesiveness, they were not subjected to the measurement of water resistance. The evaluations of these samples are expressed with a dash in the table.

The abbreviations in the Examples and the tables represent the following compounds.

P-GLY: polyglycerin #750 (number average molecular weight: 750)
P-GLY-EO450: polyglycerin ethylene oxide adduct (number average molecular weight: 450)
P-GLY-EO750: polyglycerin ethylene oxide adduct (number average molecular weight: 750)
P-GLY-EO1000: polyglycerin ethylene oxide adduct (number average molecular weight: 1000)
SOR-EO270: sorbitol ethylene oxide adduct (number average molecular weight: 270)
SOR-EO530: sorbitol ethylene oxide adduct (number average molecular weight: 530)
SOR-EO710: sorbitol ethylene oxide adduct (number average molecular weight: 710)
BPA-EO: bisphenol A ethylene oxide adduct (number average molecular weight: 400)
L-LD: L-lactide
D-LD: D-lactide
CL: ε-caprolactone
TMA: trimellitic anhydride
SC: succinic anhydride
MA: maleic anhydride
TEA: triethylamine
TETA: triethanolamine
AN: ammonia water (28%)
NaHCO3: sodium hydrogencarbonate Example A-1

Production of Polylactic Polyester Resin No. 1

8.7 parts of polyglycerin ethylene oxide adduct (number average molecular weight: 1000), 74.4 parts of L-lactide, 15.2 parts of ε-caprolactone, and 0.028 parts of tin octylate as a catalyst were placed in a 500-ml glass flask equipped with a thermometer, a stirrer, and a Liebig condenser, and nitrogen gas was made to circulate for 30 minutes at 60° C. Then, the pressure was reduced for 30 minutes at 60° C. to further dry the mixture. While nitrogen gas was made to circulate again, the polymerization system was heated to 180°. After the temperature reached 180° C., the mixture was stirred for 3 hours. Then, 0.018 parts of phosphoric acid was added and the mixture was stirred for 20 minutes. Thereafter, the system was depressurized, and unreacted lactide and caprolactone were distilled off. After about 20 minutes, the distillation of the unreacted substances was stopped, and 5.5 parts of succinic anhydride was added and stirred for 2 hours at 180° C. The resulting mixture was separated and cooled. Table 1 shows the formulation, the number average molecular weight, and the lactic acid content percentage of the resulting polylactic polyol A.

Examples A-1 to A-7 and Comparative Examples A-8 to A-15

Production of Polylactic Polyester Resins No. 2 to 15

Polylactic polyester resins No. 2 to 15 were synthesized in the same manner as in the production of polylactic polyester resin No. 1, except that the materials and their proportions were changed. Polylactic polyester resins No. 2 to 15 were evaluated in the same manner as in the evaluation of polylactic polyester resin No. 1. Tables 1 and 2 show the evaluation results.

TABLE 1

| | | | Examples | | | | | | |
|---|---|---|---|---|---|---|---|---|---|
| | | | A-1 | A-2 | A-3 | A-4 | A-5 | A-6 | A-7 |
| | Resin No. | | 1 | 2 | 3 | 4 | 5 | 6 | 7 |
| Resin formulation | Z—(O—(CH$_2$CH$_2$O)$_p$—)$_r$— | P-GLY | 0.0 | 0.0 | 0.0 | 0.0 | 0.0 | 0.0 | 0.0 |
| | | P-GLY-EO450 | 0.0 | 0.0 | 13.7 | 0.0 | 0.0 | 0.0 | 0.0 |
| | | P-GLY-EO750 | 0.0 | 0.0 | 0.0 | 0.0 | 7.9 | 0.0 | 7.9 |
| | | P-GLY-EO1000 | 8.7 | 0.0 | 0.0 | 0.0 | 0.0 | 0.0 | 0.0 |
| | | SOR-EO270 | 0.0 | 0.0 | 0.0 | 0.0 | 0.0 | 0.0 | 0.0 |
| | | SOR-EO530 | 0.0 | 8.1 | 0.0 | 0.0 | 0.0 | 5.6 | 0.0 |
| | | SOR-EO710 | 0.0 | 0.0 | 0.0 | 1.8 | 0.0 | 0.0 | 0.0 |
| | | BPA-EO | 0.0 | 0.0 | 0.0 | 0.0 | 0.0 | 0.0 | 0.0 |
| | —(CO—Y—O)$_q$— | L-LD | 73.0 | 52.2 | 43.2 | 57.8 | 70.2 | 72.0 | 67.3 |
| | | D-LD | 0.0 | 0.0 | 0.0 | 7.2 | 0.0 | 0.0 | 16.8 |
| | | CL | 14.4 | 17.4 | 36.0 | 28.9 | 13.9 | 14.2 | 0.0 |
| | —X | TMA | 0.0 | 22.3 | 0.0 | 4.3 | 8.0 | 8.2 | 8.0 |
| | | SC | 3.9 | 0.0 | 0.0 | 0.0 | 0.0 | 0.0 | 0.0 |
| | | MA | 0.0 | 0.0 | 10.0 | 0.0 | 0.0 | 0.0 | 0.0 |
| Resin property | Lactic acid content percentage (wt %) | | 73.0 | 75.0 | 43.2 | 65.0 | 70.2 | 72.0 | 84.1 |
| | Acid value (eq/ton) | | 389 | 2325 | 734 | 451 | 837 | 857 | 837 |
| | Number average molecular weight | | 11,445 | 6,530 | 3,292 | 41,334 | 9,537 | 9,463 | 9,537 |
| | Average of p | | 5.0 | 1.3 | 1.5 | 2.0 | 3.3 | 2.0 | 3.3 |
| | Average of q | | 18.1 | 5.6 | 5.1 | 46.2 | 14.5 | 9.8 | 13.9 |
| | Average of r | | 4.0 | 6.0 | 4.0 | 6.0 | 4.0 | 6.0 | 4.0 |
| | L-lactic acid residue content percentage in —(CO—Y—O)$_q$— (wt %) | | 83.5 | 75.0 | 54.5 | 61.5 | 83.5 | 83.5 | 80.0 |
| | Storage stability | | A | A | A | A | A | A | A |

TABLE 2

| | | | Comparative Example | | | | | | | |
|---|---|---|---|---|---|---|---|---|---|---|
| | | | A-8 | A-9 | A-10 | A-11 | A-12 | A-13 | A-14 | A-15 |
| | Resin No. | | 8 | 9 | 10 | 11 | 12 | 13 | 14 | 15 |
| Resin formulation | Z—(O—(CH$_2$CH$_2$O)$_p$—)$_r$— | P-GLY | 0.0 | 0.0 | 0.0 | 0.0 | 6.4 | 0.0 | 0.0 | 0.0 |
| | | P-GLY-EO450 | 0.0 | 0.0 | 24.4 | 0.0 | 0.0 | 0.0 | 0.0 | 0.0 |
| | | P-GLY-EO750 | 6.8 | 0.0 | 0.0 | 0.0 | 0.0 | 0.0 | 0.0 | 7.6 |
| | | P-GLY-EO1000 | 0.0 | 0.0 | 0.0 | 0.0 | 0.0 | 0.0 | 0.0 | 0.0 |
| | | SOR-EO270 | 0.0 | 0.0 | 0.0 | 0.0 | 0.0 | 0.0 | 2.7 | 0.0 |
| | | SOR-EO530 | 0.0 | 14.3 | 0.0 | 0.0 | 0.0 | 0.0 | 0.0 | 0.0 |
| | | SOR-EO710 | 0.0 | 0.0 | 0.0 | 1.3 | 0.0 | 0.0 | 0.0 | 0.0 |
| | | BPA-EO | 0.0 | 0.0 | 0.0 | 0.0 | 0.0 | 4.9 | 0.0 | 0.0 |
| | —(CO—Y—O)$_q$— | L-LD | 75.6 | 47.7 | 39.1 | 58.1 | 71.3 | 84.8 | 74.2 | 16.9 |
| | | D-LD | 0.0 | 0.0 | 9.8 | 7.3 | 0.0 | 0.0 | 0.0 | 0.0 |
| | | CL | 14.9 | 9.4 | 9.7 | 29.0 | 14.1 | 4.5 | 14.7 | 67.8 |
| | —X | TMA | 0.0 | 28.6 | 0.0 | 4.4 | 8.2 | 5.8 | 8.5 | 7.6 |
| | | SC | 2.8 | 0.0 | 0.0 | 0.0 | 0.0 | 0.0 | 0.0 | 0.0 |
| | | MA | 0.0 | 0.0 | 17.1 | 0.0 | 0.0 | 0.0 | 0.0 | 0.0 |
| Resin property | Lactic acid content percentage (wt %) | | 75.6 | 47.7 | 48.8 | 65.3 | 71.3 | 84.8 | 74.2 | 16.9 |
| | Acid value (eq/ton) | | 279 | 2979 | 1744 | 454 | 850 | 605 | 884 | 794 |
| | Number average molecular weight | | 11,042 | 3,706 | 1,843 | 54,354 | 11,705 | 8,227 | 10,130 | 9,833 |
| | Average of p | | 3.3 | 1.3 | 1.5 | 2.0 | 0.0 | 2.0 | 0.3 | 3.3 |
| | Average of q | | 18.1 | 2.6 | 2.0 | 64.2 | 6.0 | 26.6 | 10.9 | 17.5 |
| | Average of r | | 4.0 | 6.0 | 4.0 | 6.0 | 4.0 | 2.0 | 6.0 | 4.0 |
| | L-lactic acid residue content percentage in —(CO—Y—O)$_q$— wt %) | | 83.5 | 83.5 | 66.8 | 61.5 | 83.5 | 95.0 | 83.5 | 20.0 |
| | Storage stability | | A | C | A | A | A | A | A | A |

Polylactic polyester resin No. 8 has a small acid value, and thus falls out of the range of the present invention. Further, polylactic polyester resin No. 9 has a large acid value and a small q value, and thus falls out of the range of the present invention. The storage stability of resin No. 9 is inferior, presumably because it has a high acid value and high water absorbing property. Polylactic polyester resin No. 10 has a small number average molecular weight and a small q value, and thus falls out of the range of the present invention. Polylactic polyester resin No. 11 has a large number average molecular weight, and thus falls out of the range of the present invention. The average value of p of polylactic polyester resin No. 12 is 0, and thus polylactic polyester resin No. 12 falls out of the range of the present invention. Polylactic polyester resin No. 13 has a divalent organic group at the position corresponding to Z of the polylactic polyester resin of the present invention, and thus falls out of the range of the present invention. The average value of p of polylactic polyester resin No. 14 is small; thus polylactic polyester resin No. 14 falls out of the range of the present invention. Resin No. 15 has a small lactic acid content percentage, and thus cannot be regarded as a material causing a small environmental burden.

Example C-1

Production and Evaluation of Polylactic Polyester Resin Aqueous Dispersion and Aqueous Adhesive 25 parts of polylactic polyester resin No. 1, 1.0 part of TEA, and 75 parts of water were placed in a 500-ml glass flask equipped with a thermometer, a stirrer, and a Liebig condenser, and heated to 70° C. and stirred for an hour. The resulting mixture was separated and cooled, thereby producing polylactic polyester resin aqueous dispersion 1. The particle diameter of the obtained aqueous dispersion was measured. Further, a curing agent was added in the manner described above, and the adhesiveness and the water resistance of the obtained coating film were evaluated. Table 3 shows the results.

Examples C-2 to C-7

Polylactic polyester resin aqueous dispersions 2 to 7 were produced in the same manner as in Example 1, except that the materials and their proportions were changed. Further, as in Example 1, a curing agent was added to polylactic polyester resin aqueous dispersions 2 to 7, and the adhesiveness and the water resistance of the obtained coating films were evaluated. Table 3 shows the results. All aqueous dispersions had high water dispersibility, and all cured coating films had high adhesiveness and water resistance.

Comparative Examples C-8 to C-15

Production of polylactic polyester resin aqueous dispersions was attempted in the same manner as in Example 1, except that the materials and their proportions were changed. For the resins that were successfully made into aqueous dispersions, a curing agent was added in the same manner as in Example 1, and the adhesiveness and the water resistance of the obtained coating films were evaluated. Table 4 shows the results.

TABLE 3

| | | | | Examples | | | | | | |
|---|---|---|---|---|---|---|---|---|---|---|
| | | | | C-1 | C-2 | C-3 | C-4 | C-5 | C-6 | C-7 |
| Formulation | Aqueous dispersion | Resin | Type | 1 | 2 | 3 | 4 | 5 | 6 | 7 |
| | | | Parts by weight | 25 | 35 | 30 | 20 | 30 | 25 | 35 |
| | | Basic compound | Type | TEA | TETA | AN | TEA | TEA | NaHCO3 | TEA |
| | | | Parts by weight | 1.0 | 12.1 | 1.3 | 0.9 | 2.5 | 1.8 | 3.0 |
| | | Water | Parts by weight | 75 | 65 | 70 | 80 | 70 | 75 | 65 |
| | Adhesive | Curing agent | Parts by weight | 1.7 | 13.8 | 3.7 | 1.5 | 4.3 | 3.6 | 5.0 |
| Property of aqueous dispersion | | Water dispersibility | | A | A | A | A | A | A | A |
| | | Particle diameter (nm) | | 75 | <40 | <40 | 60 | <40 | <40 | <40 |
| Characteristics of adhesive | | Adhesiveness (N/cm) | | 5.8 | 4.3 | 2.7 | 7.8 | 9.8 | 8.7 | 6.5 |
| | | Water resistance (N/cm) | | 5.4 | 3.3 | 2.1 | 7.9 | 9.7 | 8.2 | 6.7 |

TABLE 4

| | | | | Comparative Examples | | | | | | | |
|---|---|---|---|---|---|---|---|---|---|---|---|
| | | | | C-8 | C-9 | C-10 | C-11 | C-12 | C-13 | C-14 | C-15 |
| Formulation | Aqueous dispersion | Resin | Type | 8 | 9 | 10 | 11 | 12 | 13 | 14 | 15 |
| | | | Parts by weight | 25 | 35 | 30 | 20 | 40 | 25 | 25 | 35 |
| | | Basic compound | Type | TEA | TETA | AN | TEA | TETA | NaHCO3 | TEA | TETA |
| | | | Parts by weight | 0.7 | 15.5 | 3.2 | 0.9 | 5.1 | 1.3 | 2.2 | 4.1 |
| | | Water | Parts by weight | 75 | 65 | 70 | 80 | 60 | 75 | 75 | 65 |
| | Adhesive | Curing agent | Parts by weight | 1.2 | 17.7 | 8.9 | 1.5 | 5.8 | 2.6 | 3.8 | 4.7 |

TABLE 4-continued

| | | Comparative Examples | | | | | | | |
|---|---|---|---|---|---|---|---|---|---|
| | | C-8 | C-9 | C-10 | C-11 | C-12 | C-13 | C-14 | C-15 |
| Property of aqueous dispersion | Water dispersibility | B | A | A | C | A | B | A | A |
| | Particle diameter (nm) | — | <40 | 110 | — | 145 | — | 120 | <40 |
| Characteristics of adhesive | Adhesiveness (N/cm) | — | 1.8 | 0.3 | — | 1.7 | — | 1.9 | 7.2 |
| | Water resistance (N/cm) | — | 0.4 | 0.5 | — | 1.8 | — | 1.8 | 6.7 |

Comparative Example C-8 had a large amount of undispersed matter even after one hour of stirring, and after another hour of stirring, dispersion was still not successful. Polylactic polyester resin No. 8 used for Comparative Example C-8 had a small acid value, and thus falls out of the range of the present invention. The low water dispersibility was presumably due to the small acid value.

Comparative Examples C-9 had insufficient water resistance, and Comparative Example C-10 had insufficient adhesiveness. Resin No. 9 used for Comparative Example C-9 had a large acid value, and thus falls out of the range of the present invention. Although a curing agent in an equivalent amount with respect to the acid value was added, the reaction of all carboxyl groups failed, and a large number of unreacted carboxyl groups remained. This presumably resulted in the insufficient water resistance. Resin No. 10 used for Comparative Example C-10 had a small molecular weight, and thus falls out of the range of the present invention. The insufficient adhesiveness was presumably due to the small cohesive force because of the small molecular weight.

Polylactic polyester resin No. 11 used for Comparative Example C-11 had almost no dispersion even after one hour of stirring. After another hour of stirring, dispersion was still not successful. Resin No. 11 had a large resin molecular weight, and thus falls out of the range of the present invention. The failure in dispersion is presumably due to the large cohesive force because of the large molecular weight.

The average value of p of resin No. 12 used for Comparative Example C-12 was 0, and thus falls out of the range of the present invention. The insufficient adhesiveness is presumably because the resin failed to form a sufficient three-dimensional crosslinked structure by the reaction with the curing agent.

Comparative Example C-13 was dispersed after one hour of stirring; however, the particle diameter was relatively large, and aggregated precipitates were generated after 12 hours. Polylactic polyester resin No. 13 used for Comparative Example C-13 had low water dispersibility presumably because there was no branched structure in the initiator, and the hydrophilic group was absent only in the resin terminal. Further, since the L-lactic acid content according to Formula (1) was 90% or more, the resin undergoes crystallization, thereby decreasing the water dispersibility.

The average value of p of resin No. 14 used for Comparative Example C-14 was small, and thus the resin falls out of the range of the present invention. The insufficient adhesiveness is presumably because the resin failed to form a sufficient three-dimensional crosslinked structure by the reaction with the curing agent.

Comparative Example C-15 had desirable performance; however, it has a small lactic acid content, and thus cannot be regarded as a material with a small environmental burden.

Paint

Production Example of Aqueous Paint (d-1)

100 parts of polylactic polyester resin No. 1, 4.0 parts of TEA, and 233 parts of water were placed in a 500-ml glass flask equipped with a thermometer, a stirrer, and a Liebig condenser, and heated to 70° C. and stirred for one hour. The mixture was separated and cooled, and filtrated with a 100-mesh filter fabric. 20 parts of a curing agent (M-40W: Sumitomo Chemical Co., Ltd.), 150 parts of ion exchanged water, 50 parts of titanium oxide (CR-93: Ishihara Sangyo Kaisha, Ltd.), and 2.5 parts of 10% sodium dodecylbenzenesulfonate in benzyl alcohol were added to the obtained filtrate, and shaken for three hours to evenly disperse the solid content by using a glass-bead high-speed shaker, thereby obtaining an aqueous paint (d-1).

Production Example of Aqueous Paint (d-2)

An aqueous paint was produced in the same manner and with the same formulation as in the production of aqueous paint (d-1), except that polylactic polyester resin No. 5 was used instead of polylactic polyester resin No. 1, and 8.3 parts of TEA was used, thereby obtaining an aqueous paint (d-2).

A coating film performance test was performed using aqueous paints (d-1) and (d-2). The production and evaluation of the coated plate were performed as follows. Table 5 shows the results.

Production of Coated Plate

After hot-dip galvanized steel plates were coated with aqueous paints (d-1) and (d-2), the plates were dried at 80° C. for 10 minutes, and then baked for 30 minutes at 140° C. The film thickness was 5 μm.

Evaluation Method

1. Glossiness

The reflection at 60° was measured using a gloss meter (Tokyo Denshoku Co., Ltd.).

A: 90 or more
B: 80 to 90
C: 50 to 80
D: 50 or less

2. Boiling Water Test

After immersing the coated steel plates in boiling water for two hours, the appearance of the coating film (generation of blister) was evaluated.

A: No blister observed.
B: Blister area was 10% or less.
C: Blister area was 10 to 50%.
D: Blister area was 50% or more.

3. Solvent Resistance

In a room kept at 20° C., a load of 1 kg/cm2 was applied on the coating surface with a gauze impregnated with methylethylketone. The gauze was moved back and forth within a 5-cm length of the surface, and kept moving until the base appeared. The number of movements back and forth was recorded. The coating surface in which the base did not appear even after 50 back and forth movements is shown as ">50". A larger number means greater superiority in curing property of the coating film.

4. Adherence

According to the JISK-5400 cross-cut tape test, 11 parallel vertical lines and 11 parallel horizontal lines perpendicular to each other were drawn on the coating film surface of a test plate with an interval of 1 mm by using a utility knife to a depth reaching the base of the plate, thereby creating a grid consisting of 100 1-mm×1-mm squares. Adhesive cellophane tape was adhered to the surface. By rapidly removing the tape, the peel-off degree of the cross-cut grid was observed and evaluated based on the following criteria.

A: Peel-off of the coating film was not observed.
B: Peel-off of the coating film was slightly observed, and 90 or more squares remained.
C: Peel-off of the coating film was observed, and not less than 50 but less than 90 squares remained.
D: Peel-off of the coating film was observed, and less than 50 squares remained.

Ink

Production Example of Aqueous Ink (e-1)

100 parts of polylactic polyester resin No. 1, 4.0 parts of TEA, and 233 parts of water were placed in a 2000-ml glass flask equipped with a thermometer, a stirrer, and a Liebig condenser, and heated to 70° C. and stirred for 1 hour. After the mixture was cooled to 30° C., 19.6 parts of iron oxide yellow aqueous dispersion (MF-5050 Yellow: Dainichiseika Color & Chemicals Mfg. Co., Ltd.), 690.2 parts of water, and 55 parts of 2-propanol were added thereto, and stirred for another hour. The mixture was separated, and filtrated with a 100-mesh filter fabric, thereby obtaining an aqueous ink (e-1).

Production Example of Aqueous Ink (e-2)

An aqueous ink was produced in the same manner with the same formulation as in the production of aqueous ink (e-1), except that polylactic polyester resin No. 5 was used instead of polylactic polyester resin No. 1, and 8.3 parts of TEA was used, thereby obtaining an aqueous ink.

An ink coating film performance test was performed using aqueous ink (e-1) and (e-2). The production and evaluation of the evaluation sample were performed as follows. Table 6 shows the results.

Evaluation of Dispersion Stability of Aqueous Ink

Aqueous ink (e-1) and aqueous ink (e-2) were stored for two weeks at 20° C. and at −5° C., and the change in the appearance of each ink was evaluated.

A: Change in appearance was not observed.
B: Almost no change in appearance was observed. (Precipitate was generated, but was redispersed by stirring.)
C: A slight amount of precipitate was generated. (A small amount of precipitate that could not be redispersed by stirring remained.)
D: Precipitate was observed.

Preparation of Water Resistance Evaluation Sample

Aqueous ink (e-1) and aqueous ink (e-2) were separately applied onto a corona-treated surface of a PET film (Toyobo Co., Ltd) having a thickness of 25 μm so that the thickness after drying was 2 μm, and dried at 80° C. for 30 minutes, thereby obtaining a water resistance evaluation sample.

Evaluation of Water Resistance

The water resistance evaluation sample was immersed in water having a temperature of 25° C. for 5 hours. After the water on the surface was wiped off, the change in appearance was confirmed.

A: Change in appearance was not observed.
B: Almost no change in appearance was observed. (A trace of water penetration was observed in a small part of the interface of the coating film and the base material.)
C: Swelling due to water was observed in part of the coating film.
D: The entire coating film was peeled off or dissolved.

Laminate

Production Example of Laminate (f-1)

100 parts of polylactic polyester resin No. 1, 4.0 parts of TEA, and 233 parts of water were placed in a 500-ml glass flask equipped with a thermometer, a stirrer, and a Liebig condenser, and heated to 70° C. and stirred for 1 hour. The mixture was cooled to a temperature of not more than 30° C., and 100 parts of colloidal silica (Snowtex-C: Nissan Chemical) was added and stirred for another hour. The mixture was filtrated with a 100-mesh filter fabric, and the obtained filtrate was applied onto a corona-treated surface of a PLA film (Innovia Films) having a thickness of 25 μm so that the thickness after drying was 5 μm, and dried at 80° C. for 30 minutes, thereby obtaining a laminate (f-1).

Production Example of Laminate (f-2)

A laminate was produced in the same manner and with the same formulation as in the production of laminate (f-1), except that polylactic polyester resin No. 5 was used instead of polylactic polyester resin No. 1, and 8.3 parts of TEA was used, thereby obtaining a laminate (f-2).

A performance test was performed using laminate (f-1) and laminate (f-2), and evaluated as follows. Table 7 shows the results.

Biomass Content

The percent by weight of biomass-derived components was calculated based on the total weight of the laminate.

Biodegradability Test

A 10-cm×10-cm laminate was placed in a composter (garbage disposal device, Mitsui Home Co., Ltd. (M A M)). After seven days, the state of sample was visually observed, and the degree of biodegradability was evaluated based on the following four criteria.

A: The original state of the sample was completely lost.
B: The original state of the sample was almost lost.
C: Some pieces of the sample remained.
D: The original state of sample was almost maintained.

Sustained-Release Biodegradable Coating Agent 100 parts of polylactic polyester resin No. 5, 8.3 parts of TEA, and 233 parts of water were placed in a 500-ml glass flask equipped with a thermometer, a stirrer, and a Liebig condenser, and heated to 70° C. and stirred for 1 hour. The mixture was cooled to a temperature of not more than 30° C., and 100 parts of colloidal silica (Snowtex-C: Nissan Chemical) was added thereto and stirred for another hour. The mixture was filtrated with a 100-mesh filter fabric, and the obtained filtrate was applied on a nitrogen-based granular fertilizer component having an average grain size of 4 mm by spraying using a jet-flow coating device. Then the moisture was evaporated by applying high-temperature hot air, thereby obtaining a sustained-release biodegradable coated body G1 in the form of coated granules.

The filtrate was also applied on a polypropylene film and dried in a hot-air drier at 60° C., and the dried film was peeled off from the polypropylene sheet, thereby obtaining a sheet of polylactic polyester resin H1 having a dried thickness of about 20 μm. The biodegradability of this sheet was evaluated in an aerobic and dark environment. The evaluation was performed according to the ASTM-D5338 method. Table 8 shows the evaluation results. It was found that the degradation speed of this sheet was higher than that of the sheet of the polylactic polyester resin H2 described later; however, it was lower than that of cellulose. The polylactic polyester resin H1 had a sustained-release property and is suitable for a coating agent and a coated body that are aimed at complete release of the object substance in a relatively short time.

Sustained-release Biodegradable Coating Agent 100 parts of polylactic polyester resin No. 7, 8.6 parts of TEA, and 233 parts of water were placed in a 500-ml glass flask equipped with a thermometer, a stirrer, and a Liebig condenser, and heated to 70° C. and stirred for 1 hour. The mixture was cooled to a temperature of not more than 30° C., and 100 parts of colloidal silica (Snowtex-C: Nissan Chemical) was added thereto and stirred for another hour. The mixture was filtrated with a 100-mesh filter fabric, and the obtained filtrate was applied on a nitrogen-based granular fertilizer component having an average grain size of 4 mm by spraying using a jet-flow coating device. Then the moisture was evaporated by applying high-temperature hot air, thereby obtaining a sustained-release biodegradable coated body G2 in the form of coated granules.

The filtrate was also applied on a polypropylene film and dried in a hot-air drier at 60° C., and the dried film was peeled off from the polypropylene sheet, thereby obtaining a sheet of polylactic polyester resin H2 having a dried thickness of about 20 μm. The biodegradability of this sheet was evaluated in an aerobic and dark environment. The evaluation was performed according to the ASTM-D5338 method. Table 8 shows the evaluation results. It was found that the degradation speed of this sheet was relatively low and is suitable for a coating agent and a coated body that are aimed at gradual release of the object substance over a relatively long time.

TABLE 5

| | | | D-1 | D-2 |
|---|---|---|---|---|
| Aqueous dispersion | Resin | Type | 1 | 5 |
| | | Parts by weight | 100 | 100 |
| | Basic compound | Type | TEA | TEA |
| | | Parts by weight | 4.0 | 8.3 |
| | Water | Parts by weight | 233 | 233 |
| Curing agent | M-40W | Parts by weight | 20 | 20 |
| Inorganic pigment | Titanium oxide (CR-93) | Parts by weight | 50 | 50 |
| Catalyst | 10% Sodium dodecylbenzenesulfonate solution | Parts by weight | 2.5 | 2.5 |
| Water | | Parts by weight | 150 | 150 |
| Solid content of paint | | wt % | 30 | 30 |
| Evaluation criteria | Glossiness | | B | A |
| | Boiling water resistance | | B | A |
| | Solvent resistance | | >50 | >50 |
| | Adherence | | B | A |

TABLE 6

| | | | E-1 | E-2 |
|---|---|---|---|---|
| Aqueous dispersion | Resin | Type | 1 | 5 |
| | | Parts by weight | 100 | 100 |
| | Basic compound | Type | TEA | TEA |
| | | Parts by weight | 4.0 | 8.3 |
| | Water | Parts by weight | 233 | 233 |
| Aqueous dispersion of pigment | MF-5050 Yellow | Parts by weight | 19.6 | 19.6 |
| Surface tension regulator | 2-propanol | Parts by weight | 55 | 55 |
| Water | | Parts by weight | 690.2 | 690.2 |
| Solid content of ink | | wt % | 10 | 10 |
| Evaluation criteria | Dispersion stability | | B | A |
| | Water resistance | | B | A |

TABLE 7

| | | | F-1 | F-2 |
|---|---|---|---|---|
| Aqueous dispersion | Resin | Type | 1 | 5 |
| | | Parts by weight | 100 | 100 |
| | Basic compound | Type | TEA | TEA |
| | | Parts by weight | 4.0 | 8.3 |
| | Water | Parts by weight | 233 | 233 |
| Filler | Snowtex-C | Parts by weight | 100 | 100 |
| Solid content | | wt % | 28 | 28 |
| Evaluation criteria | Biomass content (%) | | 94 | 93 |
| | Biodegradability | | A | A |

TABLE 8

| | Biodegradability rate (%) | | | |
|---|---|---|---|---|
| | After 10 days | After 20 days | After 30 days | After 45 days |
| Polylactic polyester resin H1 | 33 | 67 | 84 | 94 |
| Polylactic polyester resin H2 | 7 | 17 | 26 | 33 |
| Cellulose | 80 | 90 | 97 | 100 |

INDUSTRIAL APPLICABILITY

The polylactic polyester resin of the present invention can be dispersed in water by using only a basic compound and water. Thus, the present invention provides an environmentally friendly resin and aqueous dispersion. Further, by adding a curing agent to the resin, the present invention provides a coating film having high water resistance.

The invention claimed is:

1. A polylactic polyester resin having a chemical structure represented by Formula (1), an acid value of 300 to 2,500 eq/$10^6$ g, and a number average molecular weight of 2,000 to 50,000, wherein the polylactic polyester resin contains not less than 40 weight % of lactic acid,

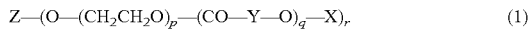 (1)

wherein Z is an r-valent organic group selected from the group consisting of polyglycerin and sorbitol, wherein Y is selected from the group consisting of —CH(CH$_3$)—, a mixture of —CH(CH$_3$)— and a linear C2-C10 alkylene group, and a mixture of —CH(CH$_3$)— and a branched C2-C10 alkylene group, wherein X is a polybasic acid having 2 or more carboxyl groups, wherein —(CO—Y—O)$_q$— is a random copolymer mainly formed of L-lactic acid and at least one selected from the group consisting of D-lactic acid and 6-hydorxycaproic acid, wherein a content percentage of L-lactic acid in the —(CO—Y—O)$_q$— is not more than 90 weight %, and wherein p, q, and r are each independently 0 or an integer, p having an average value of not less than 0.5, q having an average value of not less than 5, and r having an average value of not less than 3 and not more than 15.

2. The polylactic polyester resin according to claim 1, wherein, in Formula (1), X is selected from the group consisting of trimellitic anhydride, succinic anhydride, and maleic anhydride.

3. A polylactic polyester resin aqueous dispersion comprising the polylactic polyester resin of claim 1, a basic compound, and water.

4. The polylactic polyester resin aqueous dispersion according to claim 3, wherein the polylactic polyester resin aqueous dispersion does not comprise a surfactant.

5. The polylactic polyester resin aqueous dispersion according to claim 3, wherein the polylactic polyester resin aqueous dispersion does not comprise an organic solvent.

6. A method for producing a polylactic polyester resin aqueous dispersion, comprising mixing the polylactic polyester resin of claim 1, a basic compound, and water, without adding a surfactant or organic solvent.

7. An aqueous resin composition comprising the polylactic polyester resin of claim 1, and a curing agent having a reactivity with a carboxyl group.

8. The aqueous resin composition according to claim 7, wherein the curing agent is at least one selected from the group consisting of polyvalent epoxy compounds, oxazoline resins, carbodiimide resins, and polyvalent metal salts.

9. An aqueous adhesive comprising the aqueous resin composition of claim 7.

10. An aqueous paint comprising the aqueous resin composition of claim 7.

11. An aqueous ink comprising the aqueous resin composition of claim 7 and a colorant material.

12. A laminate comprising a layer A having the polylactic polyester resin of claim 1, and a layer B selected from the group consisting of films, sheets, woven fabric, non-woven fabric, and paper.

13. The laminate according to claim 12, wherein the Layer B mainly comprises a biomass-derived substance and/or an chemically modified biomass-derived substance.

14. A packaging material comprising the laminate of claim 12.

15. A sustained-release biodegradable coating agent comprising the aqueous resin composition of claim 7.

16. A sustained-release biodegradable coated body in which an object substance is coated with the sustained-release biodegradable coating agent according to claim 15.

17. The sustained-release biodegradable coated body according to claim 16, wherein the object substance is a substance having at least one function selected from insecticide, herbicide, sterilization, fungicide, organism attraction, and organism repellency.

18. The sustained-release biodegradable coated body according to claim 16, wherein the object substance has at least one function selected from bioactivity, growth acceleration, and alimentation to an organism.

* * * * *